(12) United States Patent
Do Valle et al.

(10) Patent No.: US 11,081,611 B2
(45) Date of Patent: Aug. 3, 2021

(54) PHOTODETECTOR ARCHITECTURES FOR EFFICIENT FAST-GATING COMPRISING A CONTROL SYSTEM CONTROLLING A CURRENT DRAWN BY AN ARRAY OF PHOTODETECTORS WITH A SINGLE PHOTON AVALANCHE DIODE

(71) Applicant: HI LLC, Los Angeles, CA (US)

(72) Inventors: Bruno Do Valle, Brighton, MA (US); Ryan Field, Culver City, CA (US); Jacob Dahle, Arlington, MA (US); Rong Jin, Acton, MA (US); Sebastian Sorgenfrei, Playa Vista, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/852,183

(22) Filed: Apr. 17, 2020

(65) Prior Publication Data
US 2020/0373452 A1 Nov. 26, 2020

Related U.S. Application Data

(60) Provisional application No. 62/889,999, filed on Aug. 21, 2019, provisional application No. 62/851,071, filed on May 21, 2019.

(51) Int. Cl.
*H01L 31/107* (2006.01)
*H01L 27/144* (2006.01)
*H01L 31/02* (2006.01)

(52) U.S. Cl.
CPC ........ *H01L 31/107* (2013.01); *H01L 27/1446* (2013.01); *H01L 31/02027* (2013.01)

(58) Field of Classification Search
CPC ............. H01L 31/02027; H01L 31/107; A61B 5/0042; A61B 5/24; A61B 5/4064; A61B 5/6868; G01J 2001/40
USPC ................................ 250/214 R, 208.1, 214.1
See application file for complete search history.

(56) References Cited

U.S. PATENT DOCUMENTS

| 4,963,727 | A | 10/1990 | Cova |
| 5,090,415 | A | 2/1992 | Yamashita |
| 5,853,370 | A | 12/1998 | Chance et al. |
| 5,929,982 | A | 7/1999 | Anderson |
| 6,240,309 | B1 | 5/2001 | Yamashita et al. |

(Continued)

FOREIGN PATENT DOCUMENTS

| EP | 3419168 | 12/2018 |
| WO | 2008144831 | 12/2008 |

(Continued)

OTHER PUBLICATIONS

International Search Report and Written Opinion received in International Application No. PCT/US2018/058580 dated Feb. 12, 2019.

(Continued)

*Primary Examiner* — Que Tan Le
(74) *Attorney, Agent, or Firm* — ALG Intellectual Property, LLC

(57) ABSTRACT

An exemplary system includes an array of photodetectors and a control system. Each photodetector of the array of photodetectors may include a single-photon avalanche diode (SPAD) and a fast-gating circuit configured to arm and disarm the SPAD. The control system is configured to control a current drawn by the array of photodetectors.

37 Claims, 11 Drawing Sheets

(56) References Cited

U.S. PATENT DOCUMENTS

| | | |
|---|---|---|
| 6,384,663 B2 | 5/2002 | Cova et al. |
| 6,541,752 B2 | 4/2003 | Zappa et al. |
| 6,683,294 B1 | 1/2004 | Herbert et al. |
| 7,507,596 B2 | 3/2009 | Yaung et al. |
| 7,547,872 B2 | 6/2009 | Niclass et al. |
| 7,705,284 B2 | 4/2010 | Inoue et al. |
| 8,026,471 B2 | 9/2011 | Itzler |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,633,431 B2 | 1/2014 | Kim |
| 8,754,378 B2 | 6/2014 | Prescher et al. |
| 8,817,257 B2 | 8/2014 | Herve |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | McGarvey et al. |
| 9,671,264 B2 | 6/2017 | Dandin |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| D825,112 S | 8/2018 | Saez |
| 10,158,038 B1 | 12/2018 | Do Valle et al. |
| 10,340,408 B1 | 7/2019 | Katnani et al. |
| 10,558,171 B2 | 2/2020 | Kondo |
| 10,594,306 B2 * | 3/2020 | Dandin ............ H01L 31/02027 |
| 2009/0012402 A1 | 1/2009 | Mintz |
| 2013/0342835 A1 | 12/2013 | Blacksberg |
| 2014/0211194 A1 | 7/2014 | Pacala et al. |
| 2015/0041625 A1 | 2/2015 | Dutton |
| 2015/0077279 A1 | 3/2015 | Song |
| 2015/0192677 A1 | 7/2015 | Yu et al. |
| 2015/0293224 A1 | 10/2015 | Eldada et al. |
| 2015/0364635 A1 | 12/2015 | Bodlovic et al. |
| 2016/0049765 A1 | 2/2016 | Eldada |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0218236 A1 | 7/2016 | Dhulla et al. |
| 2016/0278715 A1 | 9/2016 | Yu et al. |
| 2016/0287107 A1 | 10/2016 | Szabados |
| 2016/0341656 A1 | 11/2016 | Lu et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0118423 A1 | 4/2017 | Zhou et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2018/0003821 A1 | 1/2018 | Imai |
| 2018/0014741 A1 | 1/2018 | Chou |
| 2018/0027196 A1 | 1/2018 | Yang et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0069043 A1 | 3/2018 | Pan et al. |
| 2018/0081061 A1 | 3/2018 | Mandai et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0103528 A1 | 4/2018 | Moore |
| 2018/0366342 A1 | 12/2018 | Inoue et al. |
| 2019/0088697 A1 | 3/2019 | Furukawa et al. |
| 2019/0113385 A1 | 4/2019 | Fukuchi |

FOREIGN PATENT DOCUMENTS

| | | |
|---|---|---|
| WO | 2012135068 | 10/2012 |
| WO | 2013034770 | 3/2013 |
| WO | 2013066959 | 5/2013 |
| WO | 2015052523 | 4/2015 |
| WO | 2016166002 | 10/2016 |
| WO | 2017004663 | 1/2017 |
| WO | 2017130682 | 8/2017 |
| WO | 2017150146 | 9/2017 |
| WO | 2017203936 | 11/2017 |
| WO | 2018007829 | 1/2018 |
| WO | 2018122560 | 7/2018 |

OTHER PUBLICATIONS

International Search Report and Written Opinion received in International Application No. PCT/US2018/062777 dated Feb. 13, 2019.
Non-Final Office Action received in U.S. Appl. No, 16/177,351 dated Apr. 1, 2019.
Non-Final Office Action received in U.S. Appl. No. 16/370,991 dated Feb. 10, 2020.
Non-Final Office Action received in U.S. Appl. No. 16/537,360 dated Feb. 25, 2020.

(56) References Cited

OTHER PUBLICATIONS

Bellis, Stephen et al., "Photon counting imaging: the Digital APD," Society of Photo-Optical Instrumentation Engineers (SPIE) Conference Series, Feb. 2006, vol. 6068, pp. 111-120.

Cambie, Dario et al., "Every photon counts: understanding and optimizing photon paths in luminescent solar concentrator-based photomicroreactors (LSC-PMs)," React. Chem. Eng., 2017, 2, 561-566.

Dutton, et al., "A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5.

Lee, et al., "High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al., "A 4 X 4 X 416 digital SiPM array with 192 TDCs for multiple high-resolution timestamp acquisition," 2013 JINST 8 P05024.

Mora, Alberto D. et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

Parmesan, et al., "A 256 x 256 SPAD array with in-pixel Time to Amplitude Conversion for Fluorescence Lifetime Imaging Microscopy," 2015.

Partial Search Report received in International Application No. PCT/2020/028820.

Blutman, et al., "A 0.1 pJ Freeze Vernier Time-to-Digital Converter in 65nm CMOS," 2014 International Symposium on Circuits and Systems (ISCAS), Melbourne, Australia.

De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487.

Henderson, et al., "5.7 a 256x256 40nm/90nm CMOS 3D-Stacked 120dB Dynamic-Range Reconfigurable Time-Resolved SPAD Imager," 2019 IEEE international Solid-State Circuits Conference—(ISSCC), San Francisco, CA, USA, 2019, pp. 106-108, doi: 10.1109/ISSCC.2019.8662355.

Henderson, et al., "A 192 x 128 Time Correlated SPAD Image Sensor in 40-nm CMOS Technology," IEEE Journal of Solid-State Circuits, IEEE Journal of Solid-State Circuits, 2019.

Richardson, et al., "A 32x32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.

Fisher, et al., A Reconfigurable Single-Photon-Counting Integrating Receiver for Optical Communications, IEEE Journal of Solid-State Circuits, vol. 48, No. 7, Jul. 2013, https://www.researchgate.net/publication/260626902.

Gallivanoni, et al., Progress in Quenching Circuits for Single Photon Avalanche Diodes, IEEE Transactions on Nuclear Science, vol. 57, No. 6, Dec. 2010.

International Search Report and Written Opinion received in International Application No. PCT/US20/028820, dated Aug. 26, 2020.

International Search Report and Written Opinion received in International Application No. PCT/US20/027537, dated Sep. 7, 2020.

International Search Report and Written Opinion received in International Application No. PCT/US20/034062, dated Aug. 26, 2020.

Partial Search Report received in International Application No. PCT/US2020/027537, dated Jul. 17, 2020.

Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.

\* cited by examiner

PHOTODETECTOR ARCHITECTURES FOR EFFICIENT FAST-GATING COMPRISING A CONTROL SYSTEM CONTROLLING A CURRENT DRAWN BY AN ARRAY OF PHOTODETECTORS WITH A SINGLE PHOTON AVALANCHE DIODE

RELATED APPLICATIONS

The present application claims priority under 35 U.S.C. § 119(e) to U.S. Provisional Patent Application No 62/889,999, filed Aug. 21, 2019, and to U.S. Provisional Patent Application No. 62/851,071, filed May 21, 2019. These applications are incorporated herein by reference in their respective entireties.

BACKGROUND INFORMATION

Detecting neural activity in the brain is useful for medical diagnostics, imaging, neuroengineering, brain-computer interfacing, and a variety of other diagnostic and consumer-related applications. For example, it may be desirable to detect neural activity in the brain of a patient to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

A photodetector that employs a semiconductor-based single-photon avalanche diode (SPAD) is capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon.

In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current. However, arming an array of SPADs for a large number of light pulses, which may be typical for detecting neural activity, consumes a relatively high amount of power.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Photodetector systems with efficient fast-gating architectures are described herein. The photodetector systems described herein each include an array of photodetectors. Each array of photodetectors may include a single-photon avalanche diode (SPAD) and a fast-gating circuit configured to arm and disarm the SPAD. The photodetector system also includes a control system for controlling a current drawn by the array of photodetectors.

For example, the control system may include a plurality of switches configured to control a slew rate of the array of photodetectors. Additionally or alternatively, the control system may include a plurality of voltage sources, configured such that SPADs in the array of photodetectors may be selectively armed. Additionally or alternatively, the control system may include a switch to abstain from disarming SPADs during one or more measurement time periods while the switch is enabled. Additionally or alternatively, the control system may include a timer configured to disarm SPADs for a particular amount of time subsequent to the SPADs detecting photons.

These and other example embodiments of a control system configured to control a current drawn by the array of photodetectors are described herein. By controlling the current drawn by the array of photodetectors (e.g., decreasing the current drawn relative to a conventional photodetector system), the control system may enable the photodetector system to consume less power as compared to a conventional photodetector system. Further, controlling the current drawn by the array of photodetectors may prevent voltage ripples in inductive components that may potentially affect timing certainty and uniformity between photodetector arrays. These and other benefits and/or advantages that may be provided by the systems and methods described herein will be made apparent by the following detailed description.

Figure 1:
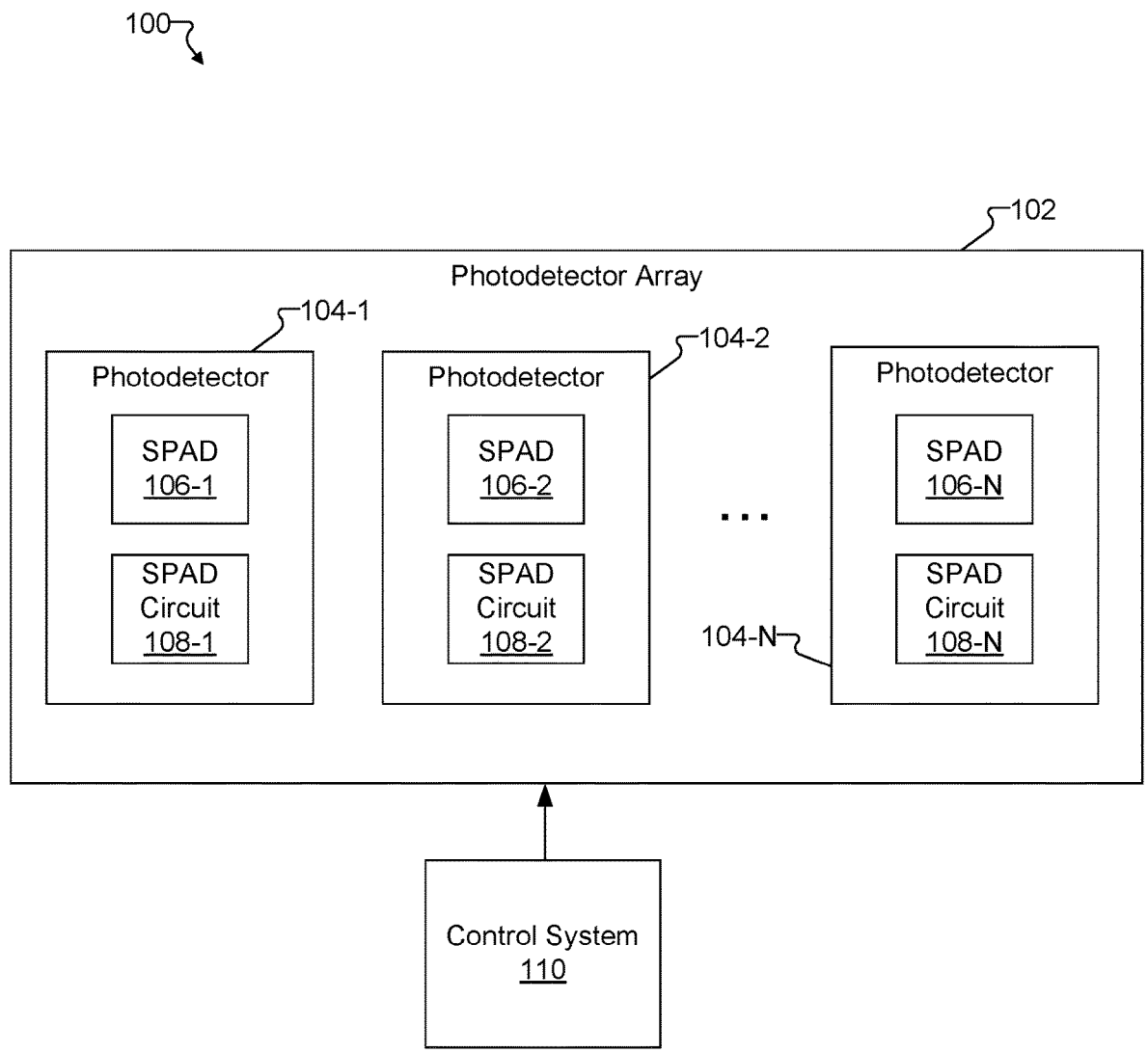
FIGS. 1-6 illustrate exemplary configurations of efficient fast-gating photodetector systems according to principles described herein.

FIG. 1 illustrates an exemplary efficient fast-gating photodetector system 100. Fast-gating photodetector system 100 shows a photodetector array 102 that includes photodetectors 104 (e.g., photodetectors 104-1 through 104-N). Each photodetector 104 includes a single-photon avalanche diode (SPAD) 106 (e.g., SPAD 106-1 through 106-N) and a SPAD circuit 108 (e.g., SPAD circuit 108-1 through 108-N) configured to control a corresponding SPAD 106. For example, photodetector 104-1 includes a SPAD 106-1 and a SPAD circuit 108-1 configured to control SPAD 102-1. Fast-gating photodetector system 100 also includes a control system 110 configured to control a current drawn by photodetector array 102. While control system 110 is shown as a separate system from photodetector array 102 in configuration 100, control system 110 or components of control system 110 may, in certain embodiments, be integrated into photodetector array 102 and/or photodetectors 104 (e.g., SPAD circuits 108). Example embodiments are described herein.

SPAD 106 may be implemented by any suitable single-photon avalanche diode configured to detect single photons. SPAD circuit 108 includes a fast-gating circuit (which may include a reset circuit) and may also include a quench circuit, implemented in any suitable manner. Example SPADs and SPAD circuits include those described in U.S. Pat. No. 10,158,038, incorporated herein by reference in its entirety.

Figure 2:
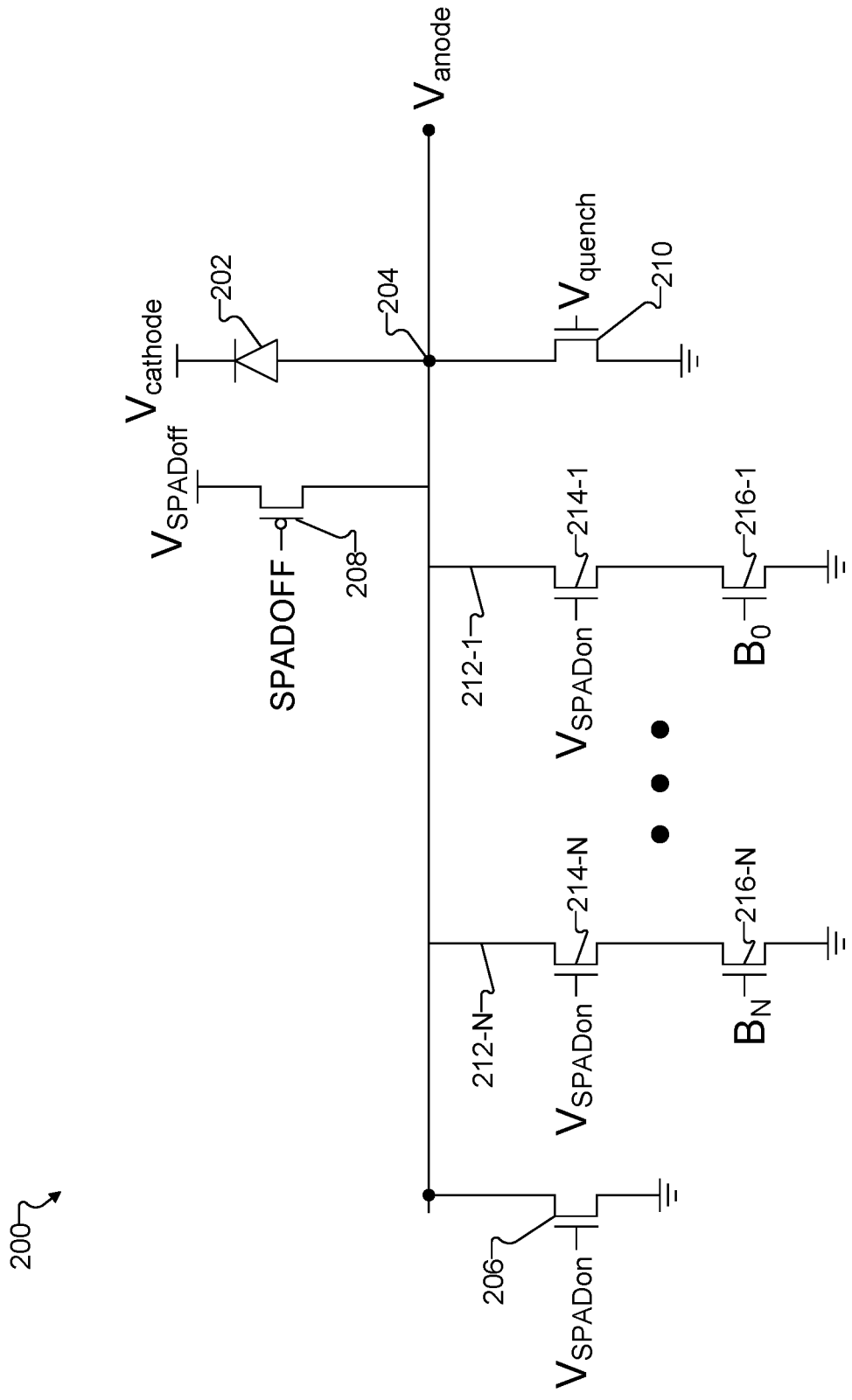

FIG. 2 illustrates an exemplary implementation 200 of fast-gating photodetector system 100. Implementation 200 shows a SPAD 202 connected at an anode 204 to a gating transistor 206, a reset transistor 208, and a quenching transistor 210. SPAD 202 implements any one of SPADs 106 (FIG. 1). Gating transistor 206, reset transistor 208, and quenching transistor 210 together (along with any other suitable components) implement any one of SPAD circuits 108 (FIG. 1). Gating transistor 206 is configured to arm SPAD 202 and is gated by a gating voltage, $V_{SPADon}$. Reset transistor 208 is configured to reset (e.g., disarm) SPAD 202 and is gated by a reset signal SPADOFF. Quenching transistor 210 is configured to control an avalanche current (e.g., a current drawn by SPAD 202 when SPAD 202 detects a photon) drawn by SPAD 202. Quenching transistor 210 is gated by a quenching voltage $V_{quench}$. In some embodiments, quenching transistor 210 may be omitted from the SPAD circuit, in which case the avalanche current may be controlled by gating transistor 206.

Implementation 200 also shows components of a control system (e.g., an implementation of control system 110) configured to control a current drawn by the SPAD circuit. The components include a plurality of branches 212 (e.g., branches 212-1 through 212-N) that are connected to anode 204 of SPAD 202 in parallel with gating transistor 206. Each branch 212 of the plurality of branches includes a switch 216 (e.g., switch 216-1 through switch 216-N, implemented in configuration 200 by transistors). Each branch 212 also includes an additional transistor 214 gated by $V_{SPADon}$.

Branches 212 are configured to control the current of the SPAD circuit by controlling a slew rate (e.g., a change in current per unit of time) of the SPAD circuit as SPAD 202 is armed and/or disarmed. Additional transistor 214 of each branch 212 may control a discharge of anode 204 of SPAD 202. Thus, the slew rate may be controlled based on switches 216. As more switches 216 are closed, the slew rate may be set to be higher. For example, a relatively fast slew rate may be set by closing switches 216 on all branches 212 (e.g., by setting B0 to BN all to high). Conversely, a relatively slow slew rate may be set by opening switches 216 (e.g., by setting B0 to BN all to low). The plurality of branches 212 may allow for a range of slew rates (e.g., between (and including) closing all switches 216 and opening all switches 216). As a result, the control system may optimize the current drawn by the SPAD circuit by setting the slew rate to a highest rate that may ensure adequate voltage ripple and data quality. Further, the control system may adapt the current drawn by the SPAD circuit based on various conditions and/or applications by opening or closing switches 216 as desired.

While implementation 200 shows each branch 212 with additional transistor 214 connected between switch 216 and anode 204 of SPAD 202, in some embodiments, transistor 214 may be connected below switch 216, such that each branch has switch 216 connected to anode 204 of SPAD 202 and transistor 214 connected between switch 216 and ground.

Figure 3:
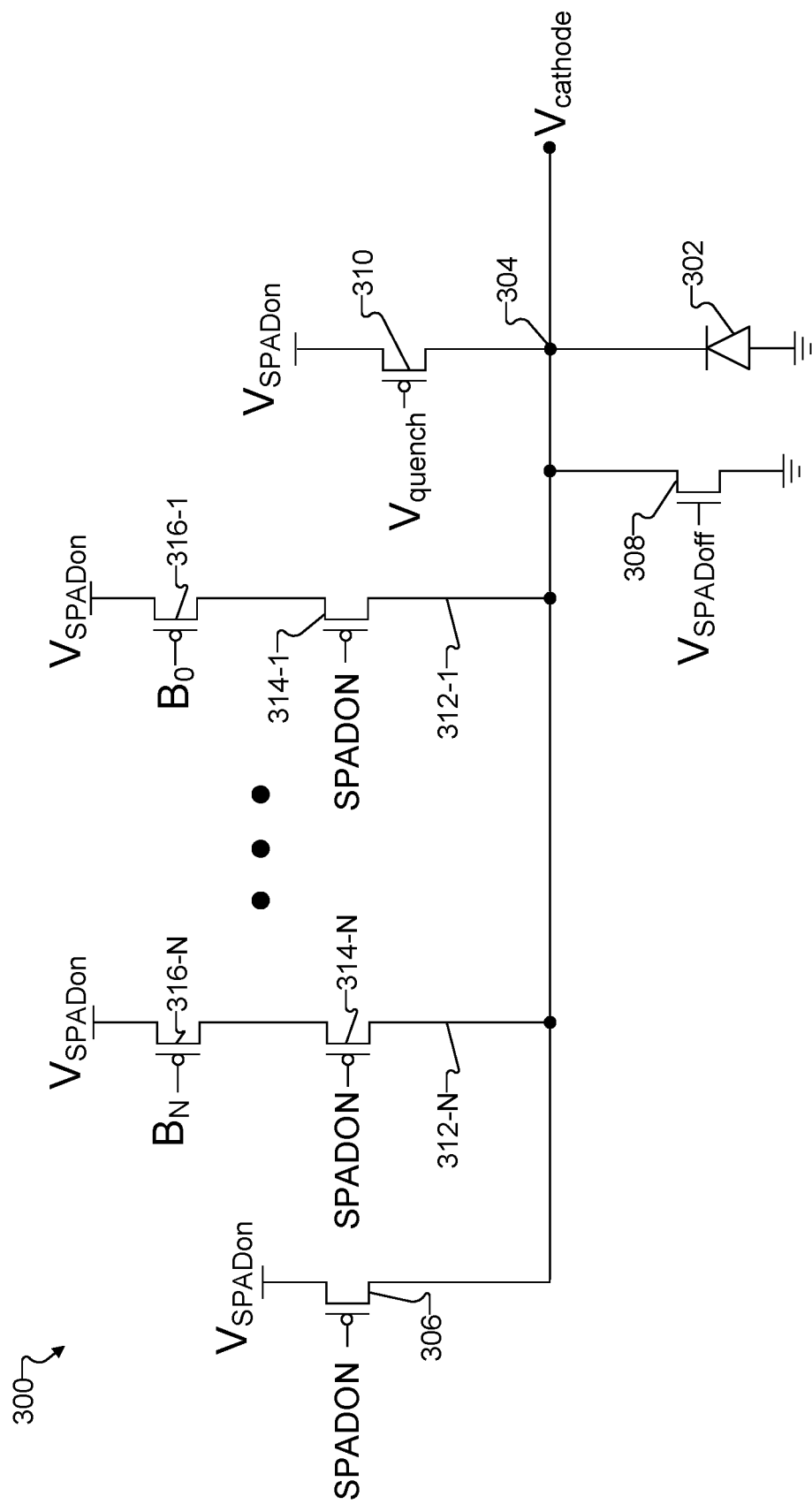

FIG. 3 illustrates another exemplary implementation 300 of fast-gating photodetector system 100. Implementation 300 is similar to implementation 200 in that implementation 300 includes a SPAD 302, a gating transistor 306, a reset transistor 308, and a quenching transistor 310. In implementation 300, gating transistor 306, reset transistor 308, and quenching transistor 310 connect to a cathode 304 of SPAD 302. SPAD 302 implements any one of SPADs 106 (FIG. 1). Gating transistor 306, reset transistor 308, and quenching transistor 310 together (along with any other suitable components) implement any one of SPAD circuits 108 (FIG. 1). Gating transistor 306 is configured to arm SPAD 302 and is gated by a gating signal, SPADON. Reset transistor 308 is configured to reset SPAD 302 and is gated by a reset signal $V_{SPADoff}$. Quenching transistor 310 is configured to control an avalanche current drawn by SPAD 302. Quenching transistor 310 is gated by a quenching voltage $V_{quench}$. In some embodiments, quenching transistor 310 may be omitted from the SPAD circuit, in which case the avalanche current may be controlled by gating transistor 306.

Implementation 300 also shows components of a control system (e.g., an implementation of control system 110) configured to control a current drawn by the SPAD circuit. The components include a plurality of branches 312 (e.g., branches 312-1 through 312-N). However, where in implementation 200, branches 212 are connected to anode 204 of SPAD 202 in parallel with gating transistor 206, in implementation 300, branches 312 are connected in parallel between cathode 304 of SPAD 302 and reset transistor 308. Otherwise, like branches 212, each branch 312 of the plurality of branches includes a switch 316 (e.g., switch 316-1 through switch 316-N, implemented in implementation 300 by transistors). Each branch 312 also includes an additional transistor 314 gated by SPADON.

Branches 312 may be configured to control a slew rate of the SPAD circuit in a similar manner as branches 212 control the slew rate of the SPAD circuit in implementation 200. Additionally, as with implementation 200, in some embodiments switch 314 and additional transistor 316 may be switched in placement order on each branch 312. Additionally, in some embodiments, the control system may include both pluralities of branches 212 and branches 312 to control the current drawn by the SPAD circuit.

Figure 4:
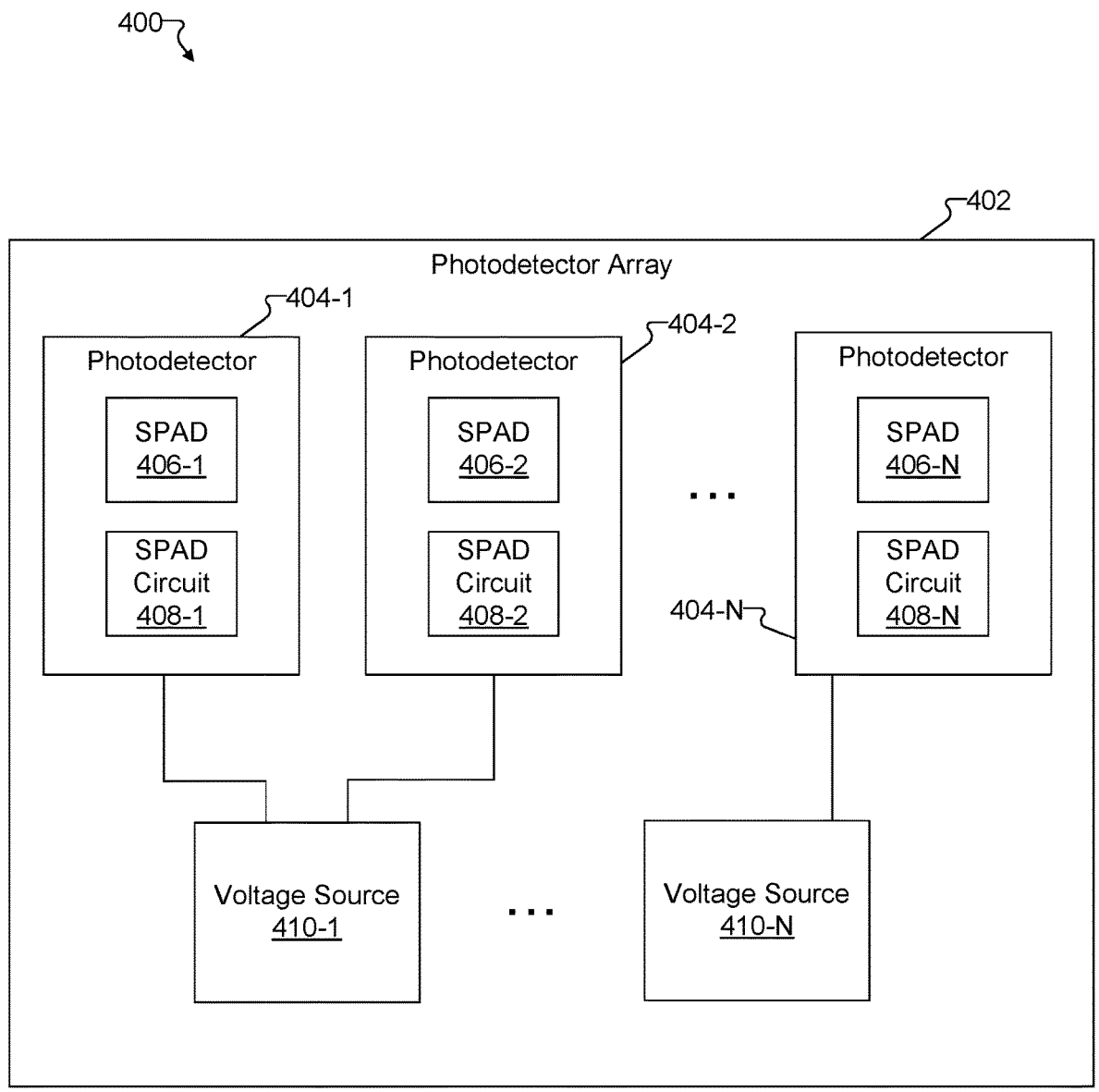

FIG. 4 illustrates another exemplary implementation 400 of fast-gating photodetector system 100 (FIG. 1). Implementation 400 includes a photodetector array 402 that includes photodetectors 404 (e.g., photodetectors 404-1 through 404-N). Each photodetector 404 includes a single-photon avalanche diode (SPAD) 406 (e.g., SPAD 406-1 through 406-N) and a SPAD circuit 408 (e.g., SPAD circuit 408-1 through 408-N). For example, photodetector 404-1 includes a SPAD 406-1 and a SPAD circuit 408-1.

Implementation 400 also includes components of a control system (e.g., an implementation of control system 110) configured to control a current drawn by photodetector array 402. The components include a plurality of voltage sources 410 (e.g., voltage source 410-1 through 410-N). Photodetectors 404 may each be connected to a voltage source 410 of the plurality of voltage sources. Thus, photodetector array 402 may be divided into subarrays, based on subsets of photodetectors 404 connected to different voltage sources 410. For example, in implementation 400, a first subset of photodetectors 404 includes photodetector 404-1 and photodetector 404-2, both connected to voltage source 410-1. A second subset of photodetectors 404 includes photodetector 404-N, connected to voltage source 410-N. Voltage sources 410 may be connected to a gate of a gating transistor of a fast-gating circuit of each photodetector 404. Thus, each subset of photodetectors 404 may be configured to be armed together by each voltage source 410 to which the subset is connected.

With photodetector array 402 divided into subarrays, the control system may selectively arm subarrays. For example, the control system may arm less than all photodetectors 404 in photodetector array 402, which would lessen a current drawn by photodetector array 402 than if all photodetectors 404 were armed. Additionally or alternatively, subarrays may be armed sequentially (e.g., within a measurement time period subsequent to a light pulse). Sequentially arming subarrays may result in all photodetectors 404 being armed, but may reduce a maximum current drawn as photodetectors 404 are not all armed at once. Also, as subarrays draw current from different voltage sources, arming subarrays may result in less current drawn per voltage source and thus a reduction in power supply ripple in the photodetector system compared to arming all photodetectors 404 from one power supply.

Further, subsets of photodetectors 404 may be organized based on a characteristic of photodetectors 404 and/or a characteristic of a light pulse response of a target that photodetectors 404 are configured to measure. For instance, a first subset of photodetectors 404 may have a higher dark count rate than a second subset of photodetectors 404. As photodetectors 404 with higher dark count rates may be more susceptible to noise, the first subset of photodetectors 404 may be armed for a portion of the light pulse response where more photons are detected, such as shortly after a light pulse is directed at the target. The second subset of photodetectors 404 may be reserved for later in the light pulse response, when fewer photons are detected, and less noise is desirable. Additionally or alternatively, more subarrays of photodetectors and/or subarrays with more photodetectors may be armed for those portions of the light pulse response where a lot of photons are expected. Any such suitable characteristics of photodetectors 404 and light pulse responses may be used to organize the subarrays.

Figure 5:
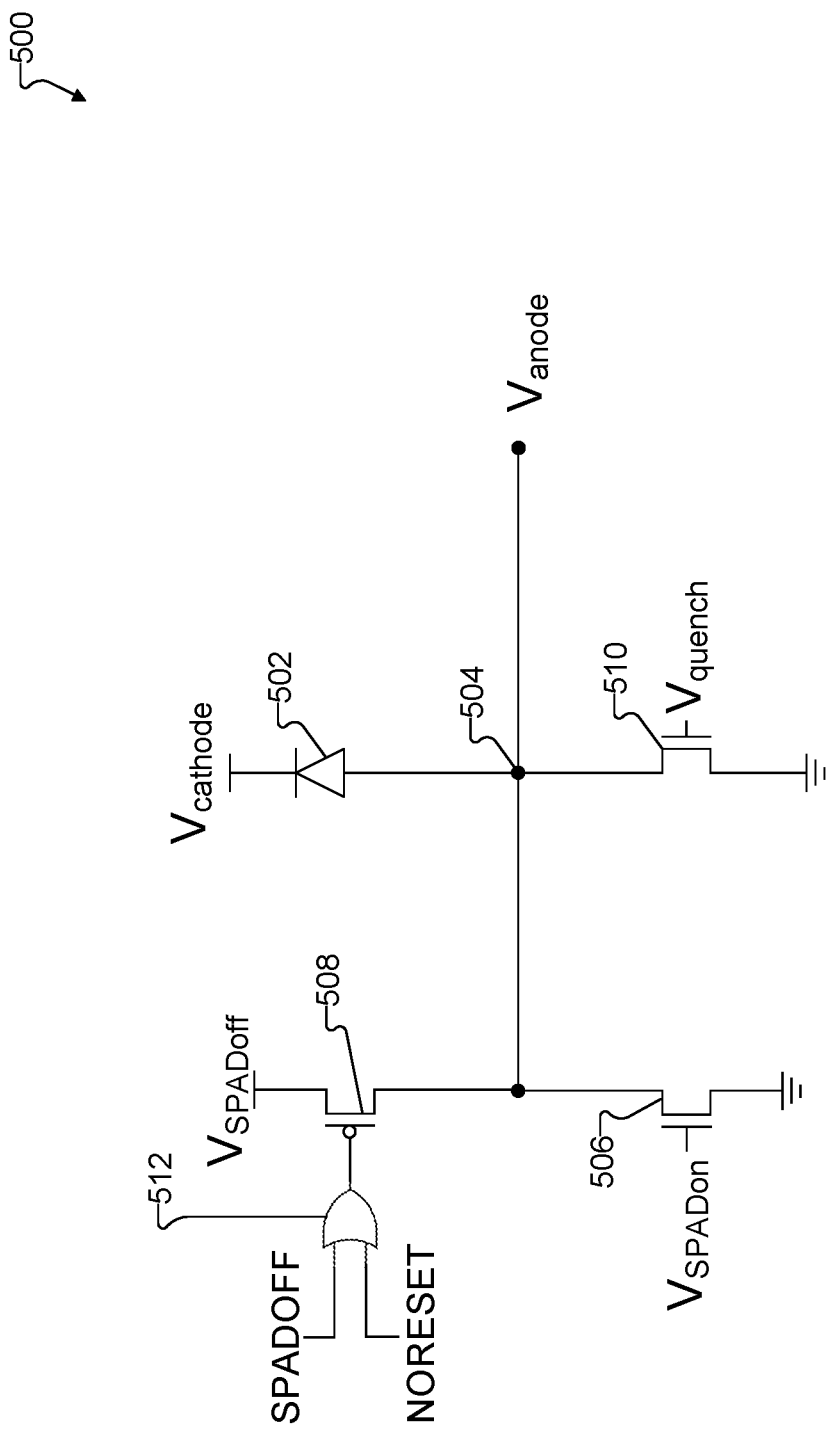

FIG. 5 illustrates another exemplary implementation 500 of fast-gating photodetector system 100 (FIG. 1). Implementation 500 includes a SPAD 502 connected at an anode 504 to a gating transistor 506, a reset transistor 508, and a quenching transistor 510. SPAD 502 implements any one of SPADs 106 (FIG. 1). Gating transistor 506, reset transistor 508, and quenching transistor 510 together (along with any other suitable components) implement any one of SPAD circuits 108 (FIG. 1). Gating transistor 506 is configured to arm SPAD 502 and is gated by a gating voltage, $V_{SPADon}$. Reset transistor 508 is configured to reset SPAD 502 and is gated by a reset signal SPADOFF. Quenching transistor 510 is configured to control an avalanche current drawn by SPAD 502. Quenching transistor 510 is gated by a quenching voltage $V_{quench}$. In some embodiments, quenching transistor 510 may be omitted from the SPAD circuit, in which case the avalanche current may be controlled by gating transistor 506.

Implementation 500 also shows a component of a control system (e.g., an implementation of control system 110) configured to control a current drawn by the SPAD circuit. The component includes an OR gate 512 coupled to a gate of reset transistor 508 to abstain from disarming SPAD 502 during one or more measurement time periods. SPAD 502 may be configured to detect photons during a measurement time period after a light pulse is directed at a target. The light pulses may be repeated many times, with a measurement time period after each one. In a conventional photodetector system, a SPAD may be reset after each measurement time period so that the SPAD may be re-armed for the next measurement time period.

In implementation 500, the control system may be configured to abstain from resetting SPAD 502. By abstaining from resetting SPAD 502, if SPAD 502 has not detected a photon for a given measurement time period, SPAD 502 does not disarm and remains armed for the next measurement time period. By not having to re-arm SPAD 502, the SPAD circuit does not draw a current that would have been drawn to arm SPAD 502. As multiple SPADs in a photodetector array may not detect photons in each measurement time period, abstaining from resetting all such SPADs may reduce an amount of current drawn by the photodetector array. If SPAD 502 does detect a photon, the SPAD circuit (e.g., quenching transistor 510) quenches SPAD 502, and then the fast-gating circuit (e.g., gating transistor 506) arms SPAD 502 for the next measurement time period.

The control system may implement abstaining from resetting using OR gate 512. By providing a high signal on a NORESET input branch of OR gate 512, an output of OR gate 512 will remain high, regardless of signals coming through SPADOFF. As a result, transistor 508 will remain open and SPAD 502 will not be reset. The NORESET signal may be a global signal that is provided to some or all of the SPADs in the photodetector array. While implementation 500 includes OR gate 512, any suitable combinational logic gate or other component may be used to provide the global NORESET signal.

When the control system is abstaining from disarming the SPADs in the photodetector array, the control system may also disregard photons detected outside a measurement time period. In some conventional photodetector systems, SPADs may be armed and disarmed so that the SPADs are only enabled to detect photons during the measurement time period. In implementation 500, however, if SPADs are not disarmed, the SPADs may detect photons outside of the measurement time period, such as photons detected directly from a light pulse, rather than after having reflected off of a target. In such instances, photons detected outside of the measurement time period may be disregarded.

Figure 6:
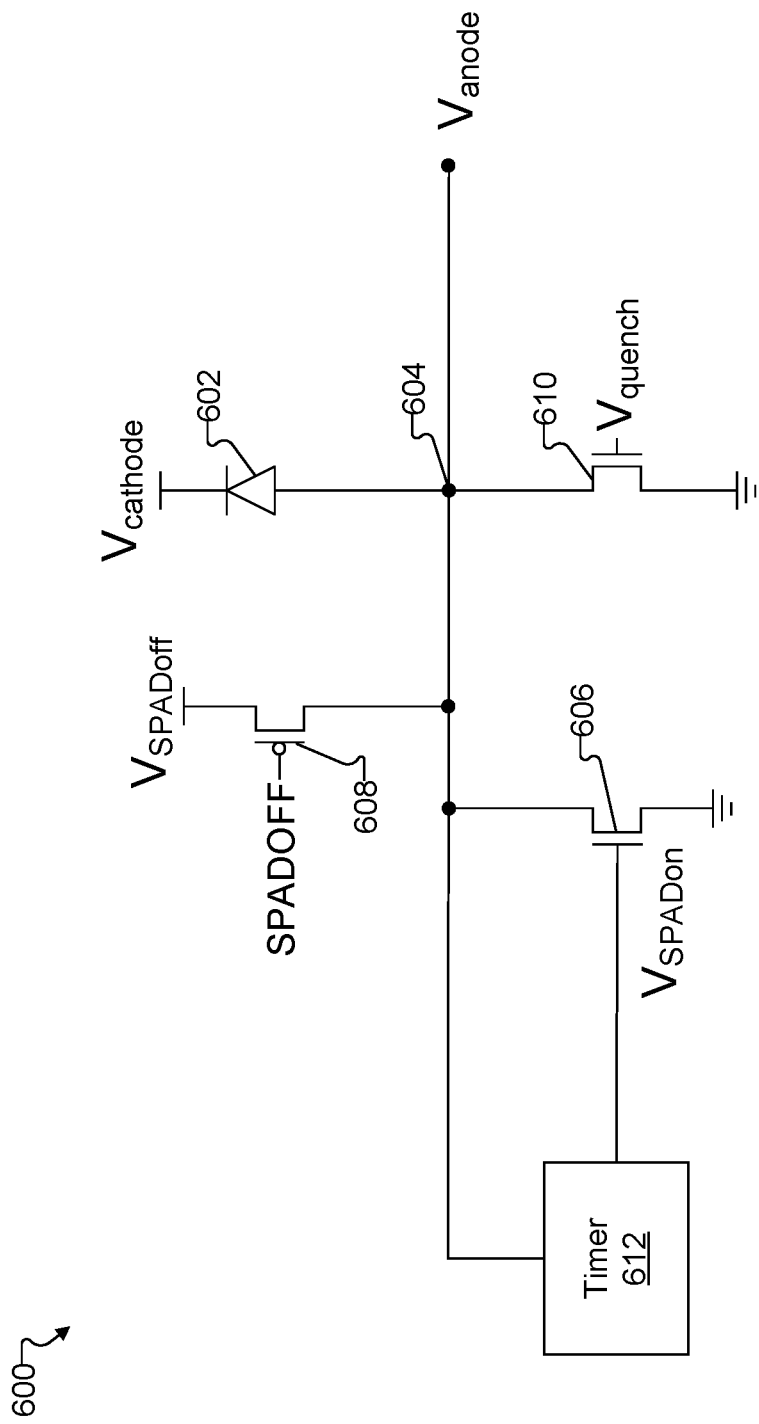

FIG. 6 illustrates another exemplary implementation 600 of fast-gating photodetector system 100 (FIG. 1). Implementation 600 includes a SPAD 602 connected at an anode 604 to a gating transistor 606, a reset transistor 608, and a quenching transistor 610. SPAD 602 implements any one of SPADs 106 (FIG. 1). Gating transistor 606, reset transistor 608, and quenching transistor 610 together (along with any other suitable components) implement any one of SPAD circuits 108 (FIG. 1). Gating transistor 606 is configured to arm SPAD 602 and is gated by a gating voltage, $V_{SPADon}$. Reset transistor 608 is configured to reset SPAD 602 and is gated by a reset signal SPADOFF. Quenching transistor 610 is configured to control an avalanche current drawn by SPAD 602. Quenching transistor 610 is gated by a quenching voltage $V_{quench}$. In some embodiments, quenching transistor 610 may be omitted from the SPAD circuit, in which case the avalanche current may be controlled by gating transistor 606.

Implementation 600 also shows a component of a control system (e.g., an implementation of control system 110) configured to control a current drawn by the SPAD circuit. The component includes a timer 612 coupled to a gate of gating transistor 606. Timer 612 is configured to disarm SPAD 602 subsequent to SPAD 602 detecting a photon until a particular point in time relative to a light pulse. By delaying a re-arming of SPAD 602 and enforcing a dead time, the control system may prevent current being drawn by the SPAD circuit by a double-triggering event. While implementation 600 shows timer 612 coupled to the gate of gating transistor 606, in other implementations, timer 612 may be coupled to other components of the SPAD circuit. For example, timer 612 may be coupled to resent transistor 608 or any other suitable component.

Figure 7A:
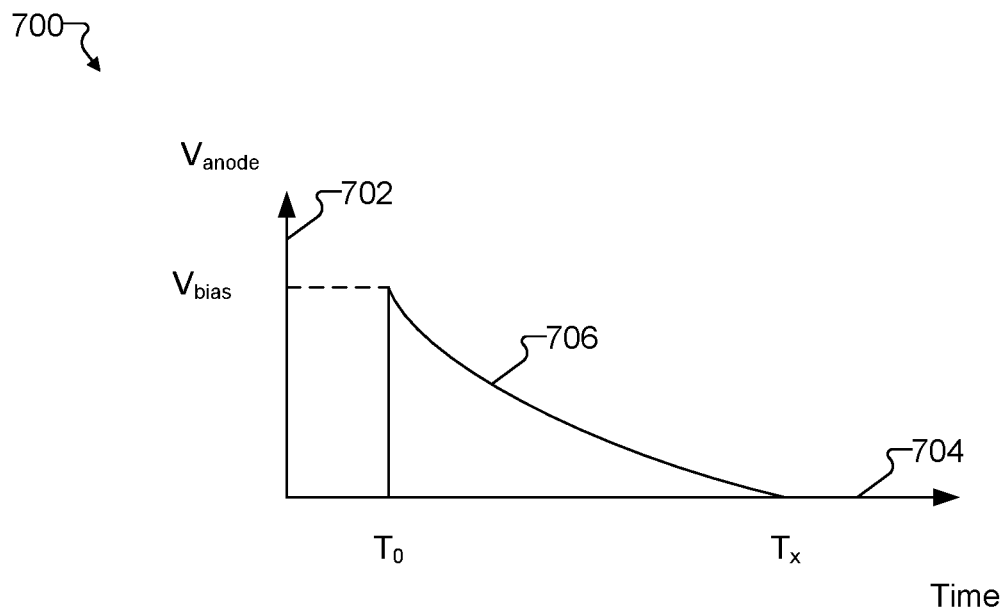
FIG. 7A illustrates an exemplary timing diagram for a conventional photodetector system.

A double-triggering event may occur when SPAD 602 detects a first photon and in a subsequent time period while anode 604 of SPAD 602 discharges to ground, SPAD 602 detects a second photon. A potential timing for such an event is shown in FIG. 7A, which illustrates an exemplary timing diagram 700 for a conventional photodetector system. Timing diagram is described with reference to SPAD 602, though configuration 600 is not a conventional photodetector system. Timing diagram 700 shows on a y-axis 702 a voltage measurement at anode 604, $V_{anode}$, of SPAD 602 mapped against time on an x-axis 704. A voltage curve 706 shows a change in voltage at anode 604 when SPAD 602 detects a photon. At time $T_0$, SPAD 602 detects a photon, SPAD 602 fires and $V_{anode}$ increases from 0 to an excess bias voltage, $V_{bias}$. The excess bias voltage is equal to a cathode voltage ($V_{cathode}$) of SPAD 602 minus a breakdown voltage of SPAD 602.

From time $T_0$, quench transistor 610 limits an amount of current flowing through SPAD 602 and starts to discharge anode 604 to ground, as shown in the decrease in voltage curve 706 from time $T_0$ to time $T_x$. A value of time $T_x$ is determined by a value of $V_{quench}$, as time $T_x$ is inversely proportional to $V_{quench}$. While $V_{anode}$ is discharging to ground, between times $T_0$ and $T_x$, a voltage across SPAD 602 is still greater than the breakdown voltage. As a result, SPAD 602 may fire again if SPAD 602 detects another photon. Many parameters of SPAD 602 (e.g., a photon detection probability (PDP), a dark current, after pulsing, etc.) may be dependent on the voltage across SPAD 602 when SPAD 602 fires. But as an exact voltage of SPAD 602 between times $T_0$ and $T_x$ may be indeterminate, a second firing (double-triggering event) of SPAD 602 may result in unexpected parameters and characteristics. Consequently, the second firing may draw more current without providing useful information.

Figure 7B:
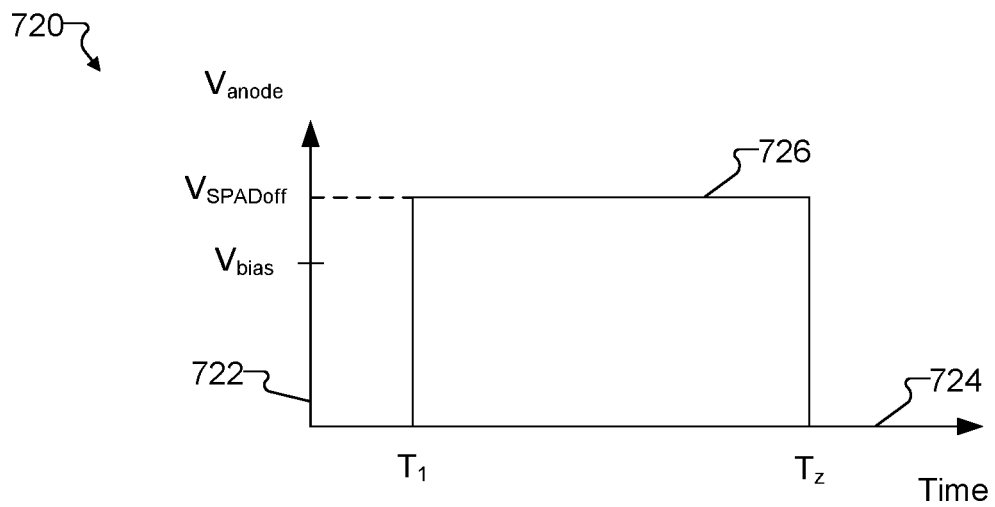
FIG. 7B illustrates an exemplary timing diagram for an efficient fast-gating photodetector system according to principles described herein.

FIG. 7B illustrates an exemplary timing diagram 720 for an efficient fast-gating photodetector architecture, such as configuration 600. Timing diagram 720 shows on a y-axis 722 a voltage measurement at anode 604, $V_{anode}$, of SPAD 602 mapped against time on an x-axis 724. A voltage curve 726 shows a change in voltage at anode 604 when SPAD 602 detects a photon, with the control system implementing timer 612. At time $T_1$, SPAD 602 detects a photon, SPAD 602 fires and SPAD 602 is then disarmed by setting $V_{anode}$ to a value greater than $V_{bias}$, such as $V_{SPADoff}$. $V_{anode}$ may be kept at $V_{SPADoff}$ until timer 612 reaches a time $T_z$. A value of time $T_z$ may be based on a predetermined amount of time from $T_1$ and/or a predetermined amount of time relative to a light pulse. For example, time $T_z$ may be set to a time after a light pulse subsequent to SPAD 602 detecting the photon. By setting time $T_z$ to after the subsequent light pulse, SPAD 602 may avoid detecting photons directly from the subsequent light pulse and instead be armed for a measurement time period after the subsequent light pulse (e.g., after the subsequent light pulse reflects off of a target).

While timing diagrams 700 and 720 show an anode voltage of a SPAD changing with respect to time, in other implementations, an anode of the SPAD may be connected to ground and a cathode voltage of the SPAD may be changing with respect to time. Such implementations may analogously use a timer to control a current drawn by a SPAD circuit.

While each of implementations 200, 300, 400, 500, and 600 have been described independently of each other, some embodiments of the control system may combine components of any or all implementations 200 through 600.

Figure 8:
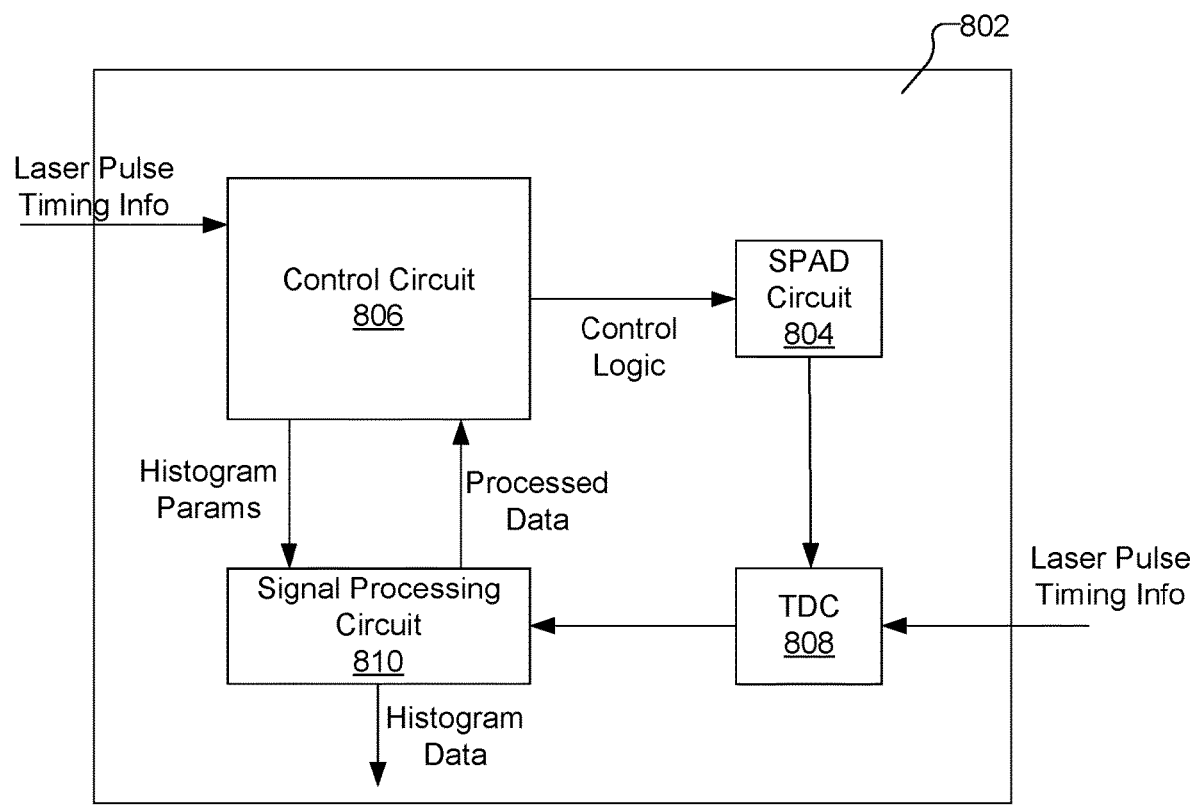
FIG. 8 illustrates an exemplary photodetector of an efficient fast-gating photodetector system according to principles described herein.

FIG. 8 illustrates various components included in an exemplary fast-gated photodetector 802. As shown, photodetector 802 includes a SPAD circuit 804, a control circuit 806, a time-to-digital converter (TDC) 808, and a signal processing circuit 810.

SPAD circuit 804 may include a SPAD and various other electrical components configured to operate together to detect a photon incident upon the SPAD. As will be described below, SPAD circuit 804 may generate an output pulse when SPAD circuit 804 detects a photon. Various implementations of SPAD circuit 804 will be described in detail below.

Control circuit 806 may be implemented by an application specific integrated circuit (ASIC) or any other suitable circuit configured to control an operation of various components within SPAD circuit 804. For example, as will be described in more detail below, control circuit 806 may output control logic that controls an operation of one or more switches within SPAD circuit 804 to selectively charge a capacitor within SPAD circuit 804 and put the SPAD included in the SPAD circuit 804 in either an armed or a disarmed state. In some examples, control circuit 806 may control a gate delay, which specifies a predetermined amount of time control circuit 806 is to wait after an occurrence of a light pulse (e.g., a laser pulse) to put the SPAD in the armed state. To this end, control circuit 806 may receive light pulse timing information, which indicates a time at which a light pulse occurs (e.g., a time at which the light pulse is applied to tissue within the brain). Control circuit 806 may also control a programmable gate width, which specifies how long the SPAD is kept in the armed state before being disarmed.

Control circuit 806 is further configured to control signal processing circuit 810. For example, control circuit 806 may provide histogram parameters to signal processing circuit 810. Signal processing circuit 810 may generate histogram data in accordance with the histogram parameters.

TDC 808 is configured to measure a time difference between an occurrence of an output pulse generated by SPAD circuit 804 and an occurrence of a light pulse. To this end, TDC 808 may also receive the same light pulse timing information that control circuit 806 receives. TDC 808 may be implemented by any suitable circuitry as may serve a particular implementation.

Signal processing circuit 810 is configured to perform one or more signal processing operations on data output by TDC 808. For example, signal processing circuit 810 may generate histogram data based on the data output by TDC 808 and in accordance with histogram parameters provided by control circuit 806. To illustrate, signal processing circuit

810 may generate, store, transmit, compress, analyze, decode, and/or otherwise process histograms based on the data output by TDC 808. In some examples, signal processing data 810 may provide processed data to control circuit 806, which may use the processed data in any suitable manner.

Figure 9A:
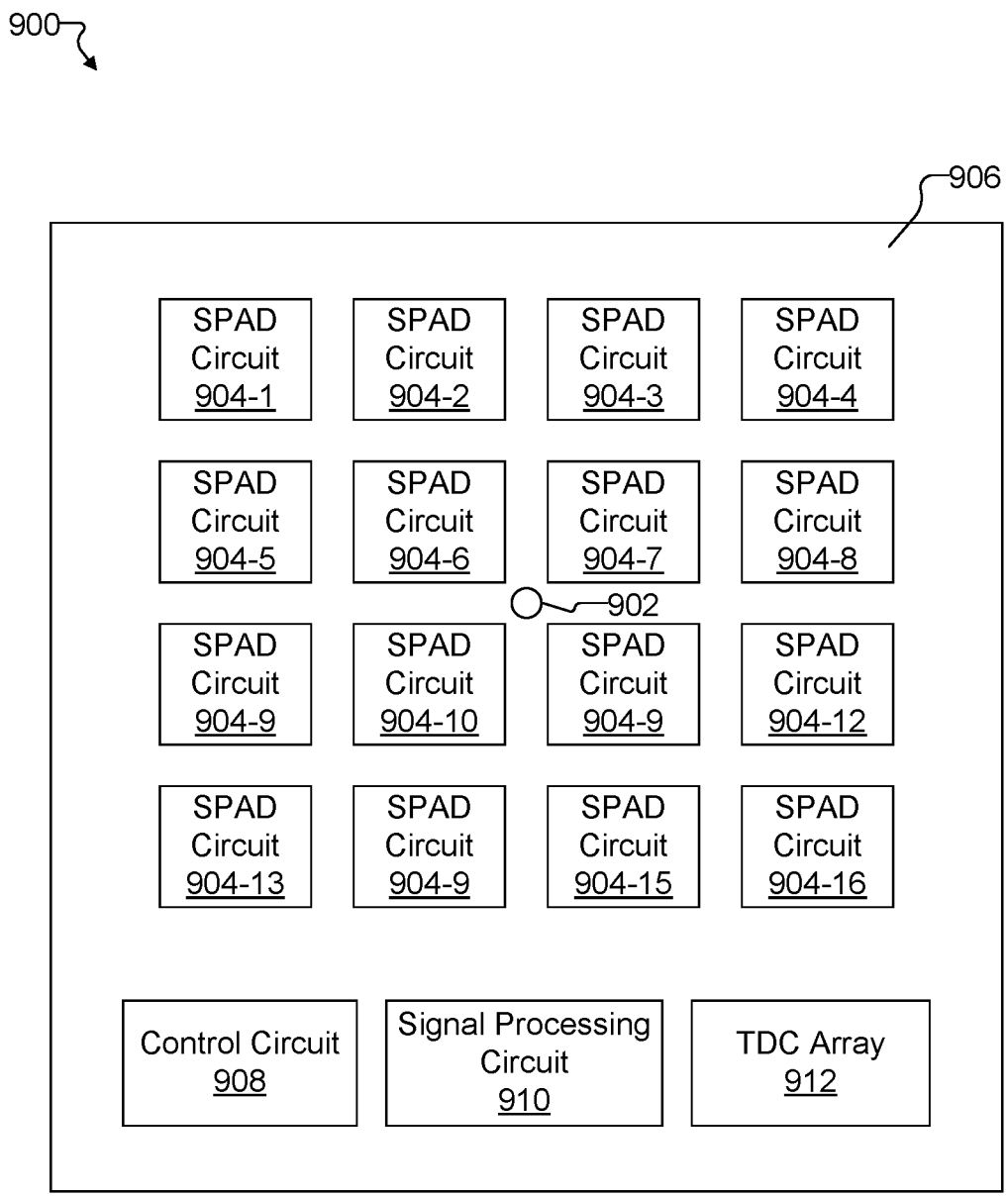
FIG. 9A illustrates an exemplary photodetector array of an efficient fast-gating photodetector system according to principles described herein.

FIG. 9A illustrates an exemplary photodetector system 900 that may be used in accordance with the systems and methods described herein. Photodetector system 900 may implement any of the photodetector systems described herein. As shown, photodetector system 900 includes a light source 902 and a plurality of SPAD circuits 904 (e.g., SPAD circuits 904-1 through 904-16) disposed on a printed circuit board (PCB) 906. Alternatively, SPAD circuits 904 (and the other components of photodetector system 900) may be disposed on an ASIC. Photodetector system 900 further includes a control circuit 908 common to SPADs 904, a signal processing circuit 910 common to SPADs 904, and a TDC array 912 that includes a plurality of TDCs each corresponding to one of the SPAD circuits 904. Control circuit 908, signal processing circuit 910, and TDC array 912 may each be disposed on PCB 906, as shown in FIG. 9A, or located elsewhere within photodetector system 900. Each SPAD circuit 904 in combination with a TDC included in TDC array 912, control circuit 908, and signal processing circuit 904 may implement a particular photodetector. Hence, photodetector system 900 may be said to include an array of photodetectors.

Light source 902 may be configured to generate one or more light pulses at one or more wavelengths that may be applied to a desired target (e.g., a target within the brain). Light source 902 may be implemented by any suitable combination of components. For example, light source 902 may be implemented by a laser source that generates laser pulses. Light source may be implemented on PCB 906 or external to PCB 906.

SPAD circuits 904 are each similar in operation to SPAD circuit 804 and may be configured to detect photons of a light pulse generated by light source 902 after the photons reflect or scatter from a target (e.g., a target internal to a user, such as brain tissue). SPAD circuits 904 may also be used to detect photons reflected from any object due to ambient light for imaging applications. In this case, light source 902 is not needed since the photons are generated by either ambient light or another light source.

As shown, SPAD circuits 904 are arranged in a four-by-four array on PCB 906. The positioning of each SPAD circuit 904 may correspond, for example, to a pixel within a pixel array. SPAD circuits 904 may alternatively be arranged in any suitable manner. While sixteen SPAD circuits 904 are shown in FIG. 9A, it will be recognized that any number of SPAD circuits 904 may be included in photodetector system 900.

Control circuit 908 may be similar in function to control circuit 806, and may be configured to control each of SPAD circuits 908. Signal processing circuit 910 may be similar in function to signal processing circuit 810, and may be configured to process signals output by each of SPAD circuits 904. TDC array 912 may include a plurality of TDCs each similar to TDC 808 and configured to measure a time difference between the occurrence of a light pulse 902 and output pulses generated by each of SPAD circuits 904.

Any of the photodetector systems described herein (e.g., photodetector system 100 and/or photodetector system 900) may be implemented by or included in any suitable device. For example, photodetector system 100 and/or photodetector system 900 may be included in a non-invasive wearable device that a user may wear to perform one or more diagnostic, imaging, and/or consumer-related operations.

Figure 9B:
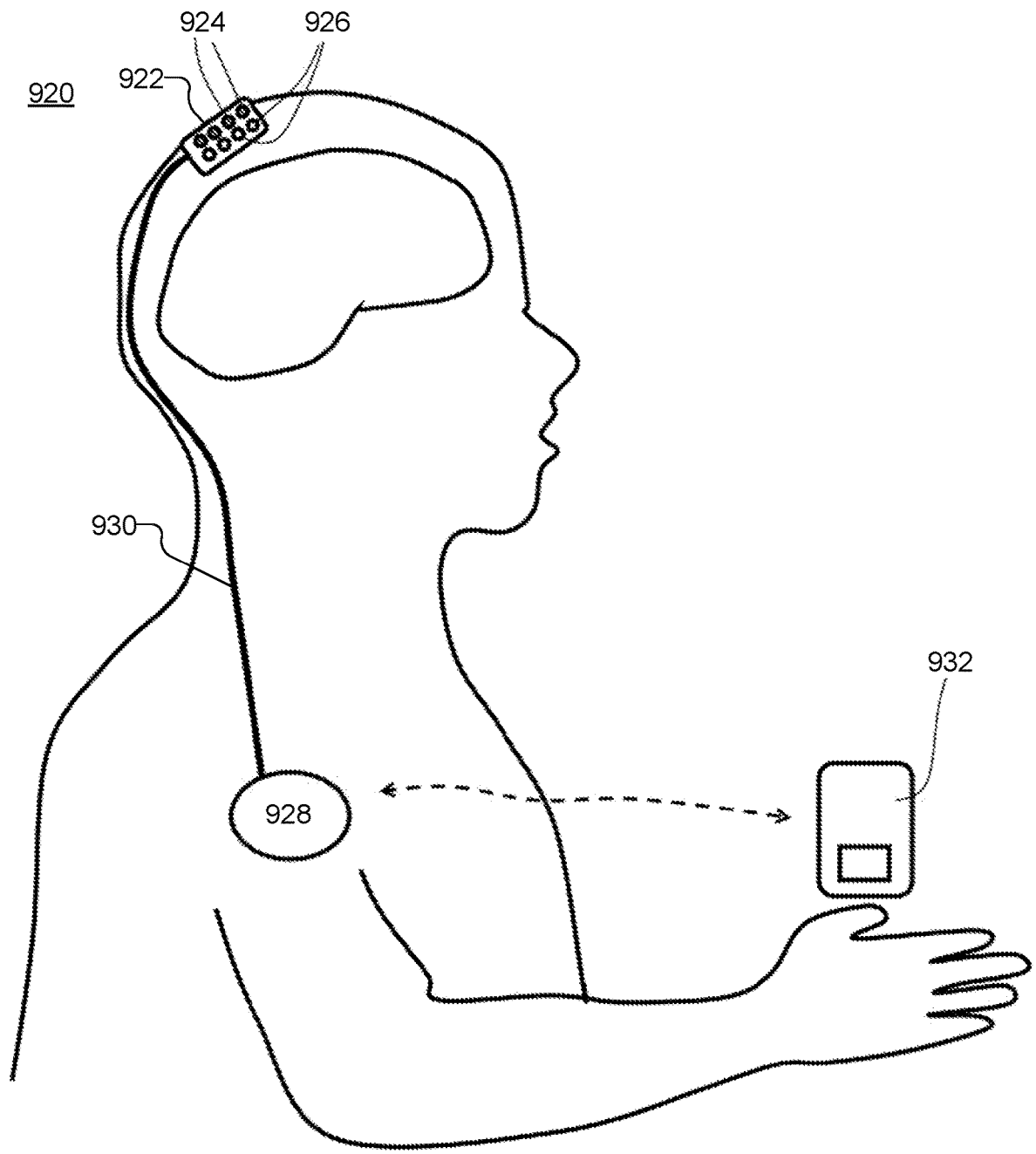
FIG. 9B illustrates an exemplary wearable device including an efficient fast-gating photodetector system according to principles described herein.

To illustrate, FIG. 9B shows an exemplary non-invasive wearable brain interface system 920 ("brain interface system 920") that implements a photodetector system, which may be similar to photodetector system 100 and/or photodetector system 900. As shown, brain interface system 920 includes a head-mountable component 922 configured to be attached to a user's head. Head-mountable component 922 may be implemented by a cap shape that is worn on a head of a user. Alternative implementations of head-mountable component 922 include helmets, beanies, headbands, other hat shapes, or other forms conformable to be worn on a user's head, etc. Head-mountable component 922 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 922 includes a plurality of photodetectors 924 and a plurality of light sources 926 configured to generate light pulses. It will be recognized that in some alternative embodiments, head-mountable component 922 may include a single photodetector 924 and/or a single light source 926. For example, brain interface system 920 may be used for controlling an optical path and for transforming photodetector pixel measurements into an intensity value that represents an optical property of a brain tissue region. Brain interface system 920 allows optical detection of deep anatomical location through skin and bone by extracting data from photons originating from light source 926 to the target location, in contrast to traditional imaging systems and methods (e.g., optical coherence tomography (OCT)), which only image superficial tissue structures or through optically transparent structures. While brain interface system 920 shows one head-mountable component 922, any suitable number of head-mountable components may be used, for instance at different locations on the head.

Brain interface system 920 may further include a processor 928 configured to communicate with (e.g., control and/or receive signals from) photodetectors 924 and light sources 926 by way of a communication link 930. Communication link 930 may include any suitable wired and/or wireless communication link. Processor 928 may include any suitable housing and may be located on the user's scalp, neck, shoulders, chest, or arm, as may be desirable. In some variations, processor 928 may be integrated in the same assembly housing as photodetectors 924 and light sources 926.

As shown, brain interface system 920 may optionally include a remote processor 932 in communication with processor 928. For example, remote processor 932 may store measured data from photodetectors 924 and/or processor 928 from previous detection sessions and/or from multiple brain interface systems (not shown). Power for photodetectors 924, light sources 926, and/or processor 928 may be provided via a wearable battery (not shown). In some examples, processor 928 and the battery may be enclosed in a single housing, and wires carrying power signals from processor 928 and the battery may extend to photodetectors 924 and light sources 926. Alternatively, power may be provided wirelessly (e.g., by induction).

In some alternative embodiments, head mountable component 922 does not include individual light sources. Instead, a light source configured to generate the light that is detected by photodetector 924 may be included elsewhere in brain interface system 920. For example, a light source may be included in processor 928 and coupled to photodetector units 924 through electrical connections.

Each of the light sources described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

Photodetector system 900 shown in FIG. 9A may alternatively be included in a non-wearable device (e.g., a medical device and/or consumer device that is placed near the head or other body part of a user to perform one or more diagnostic, imaging, and/or consumer-related operations). Photodetector system 900 may alternatively be included in a sub-assembly enclosure of a wearable invasive device (e.g., an implantable medical device for brain recording and imaging).

Any suitable SPAD circuits may be used in the photodetector architectures described herein. Some of the SPAD circuits described herein are gated with a capacitor (or, in some cases, with a parasitic capacitance of the SPAD itself) that is pre-charged with a bias voltage before a command is provided to arm the SPAD. This is described more fully in U.S. Pat. No. 10,158,038, incorporated above by reference in its entirety.

Figure 10:
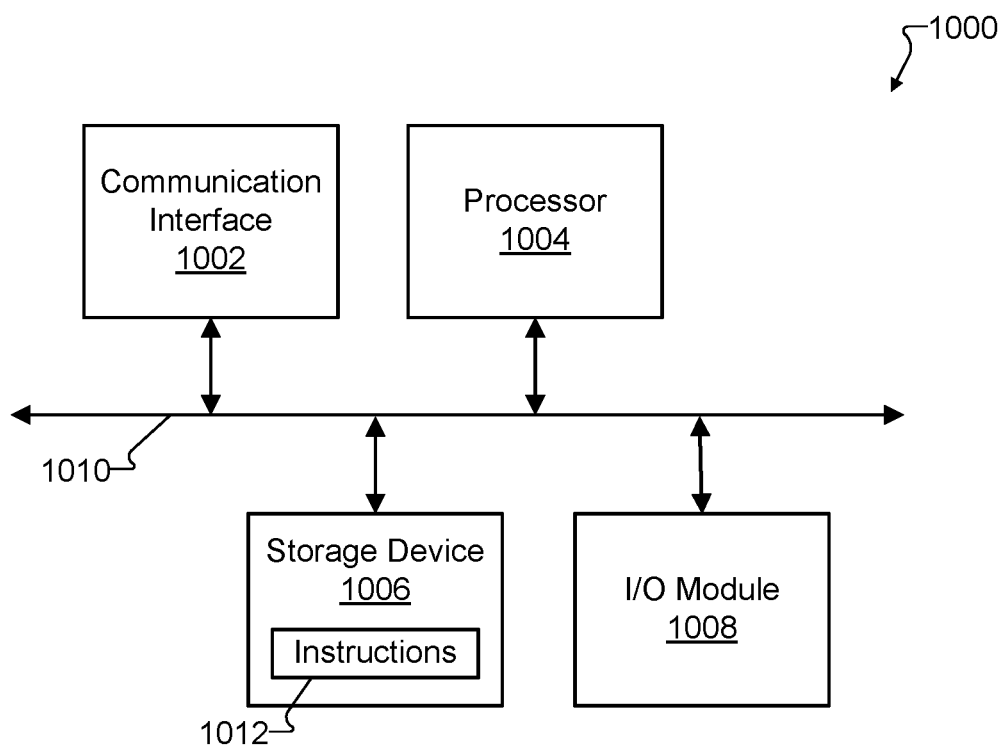
FIG. 10 illustrates an exemplary computing device according to principles described herein.

FIG. 10 illustrates an exemplary computing device 1000 that may be specifically configured to perform one or more of the processes described herein. As shown in FIG. 10, computing device 1000 may include a communication interface 1002, a processor 1004, a storage device 1006, and an input/output ("I/O") module 1008 communicatively connected one to another via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data and/or interpreting, executing, and/or directing execution of one or more of the instructions, processes, and/or operations described herein. Processor 1004 may perform operations by executing computer-executable instructions 1012 (e.g., an application, software, code, and/or other executable data instance) stored in storage device 1006.

Storage device 1006 may include one or more data storage media, devices, or configurations and may employ any type, form, and combination of data storage media and/or device. For example, storage device 1006 may include, but is not limited to, any combination of the non-volatile media and/or volatile media described herein. Electronic data, including data described herein, may be temporarily and/or permanently stored in storage device 1006. For example, data representative of computer-executable instructions 1012 configured to direct processor 1004 to perform any of the operations described herein may be stored within storage device 1006. In some examples, data may be arranged in one or more databases residing within storage device 1006.

I/O module 1008 may include one or more I/O modules configured to receive user input and provide user output. I/O module 1008 may include any hardware, firmware, software, or combination thereof supportive of input and output capabilities. For example, I/O module 1008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1000. For example, components of control system 110 may be implemented by processor 1004.

The following aspects may be considered as one or more combinations of features contemplated herein. However, the following aspects are not to be considered limiting, and more or fewer features of each combination have also been contemplated.

Aspect 1. A system comprising: an array of photodetectors comprising a first photodetector comprising: a single-photon avalanche diode (SPAD), and a fast-gating circuit configured to arm and disarm the SPAD; and a control system for controlling a current drawn by the array of photodetectors.

Aspect 2. The system of aspect 1, wherein the control system comprises a plurality of switches connected in parallel to an anode of the SPAD.

Aspect 3. The system of aspect 2, wherein: the fast-gating circuit comprises a gating transistor gated by a gating voltage, and each switch of the plurality of switches is connected to a respective additional transistor gated by the gating voltage.

Aspect 4. The system of any of aspects 2-3, wherein the control system is configured to control the amount of current drawn by controlling the plurality of switches to control a slew rate of the fast-gating circuit.

Aspect 5. The system of any of aspects 1-4, wherein the control system further comprises a quenching transistor connected in parallel with the plurality of switches, the quenching transistor configured to control an avalanche current drawn by the SPAD.

Aspect 6. The system of any of aspects 1-5, wherein the control system comprises a plurality of switches connected in parallel between an anode of the SPAD and a transistor configured to control a disarming of the SPAD; and the control system is configured to control the amount of current drawn by controlling the plurality of switches to control a slew rate of the fast-gating circuit.

Aspect 7. The system of any of aspects 1-6, wherein the control system comprises a plurality of voltage sources configured to gate a gating transistor of the fast-gating circuit; the array of photodetectors comprises: a first subset of photodetectors including the first photodetector, each photodetector of the first subset of photodetectors connected to a first voltage source of the plurality of voltage sources, and a second subset of photodetectors, each photodetector of the second subset of photodetectors connected to a second voltage source of the plurality of voltage sources; and the control system is configured control the amount of current drawn by controlling the plurality of voltage sources to selectively arm the first subset of photodetectors and the second subset of photodetectors.

Aspect 8. The system of aspect 7, wherein the first and second subsets of photodetectors are determined based on a characteristic of the photodetectors.

Aspect 9. The system of aspect 8, wherein the characteristic of the photodetectors includes a dark count, and the determining of the subsets of photodetectors includes grouping photodetectors with a larger dark count rate in the first subset of photodetectors and photodetectors with a smaller dark count rate in the second subset of photodetectors.

Aspect 10. The system of any of aspects 7-9, wherein: the array of photodetectors is configured to measure a light pulse response of a target; and the subsets of photodetectors are determined based on a characteristic of the light pulse response.

Aspect 11. The system of any of aspects 1-10, wherein the control system is configured to control the amount of current drawn by abstaining from disarming the SPAD during one or more measurement time periods.

Aspect 12. The system of aspect 11, wherein: the control system includes an OR gate coupled to a transistor of the fast-gating circuit configured to disarm the SPAD; and the control system is configured to abstain from disarming the SPAD by providing a signal to the array of photodetectors configured to keep open the transistor of the fast-gating circuit configured to disarm the SPAD.

Aspect 13. The system of any of aspects 1-12, wherein: the control system comprises a timer coupled to a gating transistor of the fast-gating circuit, the timer configured to disarm the SPAD subsequent to the SPAD detecting a photon until a particular point in time relative to a light pulse; and the control system is configured to control the amount of current drawn by controlling the timer.

Aspect 14. The system of aspect 13, wherein the timer is configured to disarm the SPAD by setting an anode voltage of the SPAD to a value greater than a difference between a cathode voltage of the SPAD and a breakdown voltage of the SPAD.

Aspect 15. The system of any of aspects 13-14, wherein the particular point in time is a time after a light pulse subsequent to the SPAD detecting the photon.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   an array of photodetectors comprising a first photodetector comprising:
   a single-photon avalanche diode (SPAD), and
   a fast-gating circuit configured to arm and disarm the SPAD; and
   a control system for controlling a current drawn by the array of photodetectors.

2. The system of claim 1, wherein the control system comprises a plurality of switches connected in parallel to an anode or a cathode of the SPAD.

3. The system of claim 2, wherein:
   the fast-gating circuit comprises a gating transistor gated by a gating voltage, and
   each switch of the plurality of switches is connected to a respective additional transistor gated by the gating voltage.

4. The system of claim 2, wherein the control system is configured to control the amount of current drawn by controlling the plurality of switches to control a slew rate of the fast-gating circuit.

5. The system of claim 2, wherein the control system further comprises a quenching transistor connected in parallel with the plurality of switches, the quenching transistor configured to control an avalanche current drawn by the SPAD.

6. The system of claim 1, wherein
   the control system comprises a plurality of switches connected in parallel between an anode or a cathode of the SPAD and a transistor configured to control a disarming of the SPAD; and
   the control system is configured to control the amount of current drawn by controlling the plurality of switches to control a slew rate of the fast-gating circuit.

7. The system of claim 1, wherein
   the control system comprises a plurality of voltage sources configured to gate a gating transistor of the fast-gating circuit;
   the array of photodetectors comprises:
     a first subset of photodetectors including the first photodetector, each photodetector of the first subset of photodetectors connected to a first voltage source of the plurality of voltage sources, and
     a second subset of photodetectors, each photodetector of the second subset of photodetectors connected to a second voltage source of the plurality of voltage sources; and
   the control system is configured control the amount of current drawn by controlling the plurality of voltage sources to selectively arm the first subset of photodetectors and the second subset of photodetectors.

8. The system of claim 7, wherein the first and second subsets of photodetectors are determined based on a characteristic of the photodetectors.

9. The system of claim 8, wherein the characteristic of the photodetectors includes a dark count, and the determining of the subsets of photodetectors includes grouping photodetectors with a larger dark count rate in the first subset of photodetectors and photodetectors with a smaller dark count rate in the second subset of photodetectors.

10. The system of claim 7, wherein:
    the array of photodetectors is configured to measure a light pulse response of a target; and
    the subsets of photodetectors are determined based on a characteristic of the light pulse response.

11. The system of claim 1, wherein the control system is configured to control the amount of current drawn by abstaining from disarming the SPAD during one or more measurement time periods.

12. The system of claim 11, wherein:
the control system includes a combinational logic gate coupled to a transistor of the fast-gating circuit configured to disarm the SPAD; and
the control system is configured to abstain from disarming the SPAD by providing a signal to the array of photodetectors configured to keep open the transistor of the fast-gating circuit configured to disarm the SPAD.

13. The system of claim 1, wherein:
the control system comprises a timer coupled to the fast-gating circuit, the timer configured to disarm the SPAD subsequent to the SPAD detecting a photon until a particular point in time relative to a light pulse; and
the control system is configured to control the amount of current drawn by controlling the timer.

14. The system of claim 13, wherein the timer is configured to disarm the SPAD by setting a voltage across the SPAD to a value smaller than a breakdown voltage of the SPAD.

15. The system of claim 13, wherein the particular point in time is a time after a light pulse subsequent to the SPAD detecting the photon.

16. The system of claim 1, wherein:
the control system comprises a plurality of switches connected in parallel to an anode or a cathode of the SPAD;
the control system is configured to control the amount of current drawn by at least one of:
controlling the plurality of switches to control a slew rate of the fast-gating circuit, and
abstaining from disarming the SPAD during one or more measurement time periods.

17. A system comprising:
an array of photodetectors comprising a first photodetector comprising:
a single photon avalanche diode (SPAD),
a fast-gating circuit configured to arm and disarm the SPAD; and
a control system comprising a plurality of switches connected in parallel to the SPAD, the control system configured to control an amount of current drawn by the array of photodetectors by controlling the plurality of switches to control a slew rate of the fast-gating circuit.

18. The system of claim 17, wherein the plurality of switches is connected to an anode or a cathode of the SPAD.

19. The system of claim 17, wherein the plurality of switches is connected between an anode or a cathode of the SPAD and a transistor configured to control disarming of the SPAD.

20. The system of claim 17, wherein:
the fast-gating circuit comprises a gating transistor gated by a gating voltage, and
each switch of the plurality of switches is connected to a respective additional transistor gated by the gating voltage.

21. The system of claim 17, wherein the first photodetector further comprises a quenching circuit connected in parallel with the plurality of switches.

22. The system of claim 17, wherein the control system is further configured to control the current drawn by abstaining from disarming the SPAD.

23. A system comprising:
an array of photodetectors comprising a first subset of photodetectors and a second subset of photodetectors, the first subset of photodetectors including a first photodetector comprising:
a single photon avalanche diode (SPAD), and
a fast-gating circuit configured to arm and disarm the SPAD;
a plurality of voltage sources including a first voltage source and a second voltage source; and
a control system configured to control an amount of current drawn by the array of photodetectors, wherein
the plurality of voltage sources are configured to gate a gating transistor of the fast-gating circuit,
the first subset of photodetectors is connected to the first voltage source,
the second subset of photodetectors is connected to the second voltage source, and
the control system is configured to control an amount of current drawn by selectively arming the first subset and the second subset of photodetectors.

24. The system of claim 23, wherein the subsets of photodetectors are determined based on a characteristic of the photodetectors.

25. The system of claim 24, wherein the characteristic of the photodetectors includes a dark count, and the determining of the subsets of photodetectors includes the first subset of photodetectors comprising photodetectors with a larger dark count rate than the second subset of photodetectors.

26. The system of claim 23, wherein:
the array of photodetectors is configured to measure a light pulse response of a target; and
the subsets of photodetectors are determined based on a characteristic of the light pulse response.

27. The system of claim 23, wherein the control system further comprises a plurality of switches connected in parallel to an anode or a cathode of the SPAD, and the control system is further configured to control the amount of current drawn by controlling the plurality of switches to control a slew rate of the fast-gating circuit.

28. The system of claim 27, wherein the control system is further configured to control the amount of current drawn by abstaining from disarming the SPAD during one or more measurement time periods.

29. The system of claim 28, wherein the control system further comprises a timer coupled to the gating transistor of the fast-gating circuit, wherein:
the timer configured to disarm the SPAD subsequent to the SPAD detecting a photon until a particular point in time relative to a light pulse, and
the control system is further configured to control an amount of current drawn by controlling the timer.

30. The system of claim 27, wherein the control system further comprises a timer coupled to the gating transistor of the fast-gating circuit, wherein:
the timer configured to disarm the SPAD subsequent to the SPAD detecting a photon until a particular point in time relative to a light pulse, and
the control system is further configured to control an amount of current drawn by controlling the timer.

31. The system of claim 23, wherein the control system further comprises a timer coupled to the gating transistor of the fast-gating circuit, wherein:
the timer configured to disarm the SPAD subsequent to the SPAD detecting a photon until a particular point in time relative to a light pulse, and
the control system is further configured to control an amount of current drawn by controlling the timer.

32. The system of claim 31, wherein the control system is further configured to control the amount of current drawn by abstaining from disarming the SPAD during one or more measurement time periods.

33. A system comprising:
an array of photodetectors comprising a first photodetector comprising:
- a single photon avalanche diode (SPAD), and
- a fast-gating circuit configured to arm and disarm the SPAD; and a control system configured to control an amount of current drawn by the array of photodetectors by abstaining from disarming the SPAD during one or more measurement time periods.

34. The system of claim 33, wherein:
the first photodetector includes a combinational logic gate coupled to a transistor of the fast-gating circuit configured to disarm the SPAD; and
the control system is configured to abstain from disarming the SPAD by providing a signal to the array of photodetectors configured to keep open the transistor of the fast-gating circuit configured to disarm the SPAD.

35. A system comprising:
an array of photodetectors comprising a first photodetector comprising:
- a single photon avalanche diode (SPAD),
- a fast-gating circuit configured to arm and disarm the SPAD; and a control system comprising a timer coupled to a gating transistor of the fast-gating circuit, the timer configured to disarm the SPAD subsequent to the SPAD detecting a photon until a particular point in time relative to a light pulse, the control system configured to control an amount of current drawn by the array of photodetectors by controlling the timer.

36. The system of claim 35, wherein the timer is configured to disarm the SPAD by setting the voltage across the SPAD less than the breakdown voltage of the SPAD.

37. The system of claim 35, wherein the particular point in time is a time after a light pulse subsequent to the SPAD detecting the photon.

* * * * *